(12) United States Patent
Cook et al.

(10) Patent No.: US 8,281,543 B2
(45) Date of Patent: Oct. 9, 2012

(54) SYSTEMS AND METHODS FOR BALLASTING COVERS FOR GAS-HOLDING SLUDGE DIGESTORS

(75) Inventors: Lynn W. Cook, Eugene, OR (US); Steven R. Hough, Junction City, OR (US); Jeffrey L. Wight, Eugene, OR (US)

(73) Assignee: Olympus Technologies, Inc., Eugene, OR (US)

( * ) Notice: Subject to any disclaimer, the term of this patent is extended or adjusted under 35 U.S.C. 154(b) by 0 days.

(21) Appl. No.: 13/186,254

(22) Filed: Jul. 19, 2011

(65) Prior Publication Data
US 2012/0042606 A1 Feb. 23, 2012

Related U.S. Application Data

(63) Continuation of application No. 12/237,348, filed on Sep. 24, 2008, now abandoned.

(51) Int. Cl.
*E04B 1/00* (2006.01)
(52) U.S. Cl. .................. 52/745.06; 220/216; 220/217
(58) Field of Classification Search ............ 52/745.06, 52/192, 19, 20, 21, 3; 210/218; 435/287, 435/289, 313–316; 220/216, 217, 220–227
See application file for complete search history.

(56) References Cited

U.S. PATENT DOCUMENTS

| | | | |
|---|---|---|---|
| 251,245 A | 12/1881 | King | |
| 1,989,589 A | 1/1935 | Fischer et al. | |
| 2,050,686 A | 8/1936 | Wiggins | |
| 2,050,915 A | 8/1936 | Beddoes et al. | |
| 2,373,797 A | 4/1945 | Willkin | |
| 3,187,897 A | 6/1965 | Walker | |
| 3,288,295 A | 11/1966 | Kelly | |
| 3,535,236 A | 10/1970 | Travis | |
| 4,060,175 A | 11/1977 | Rysgaard, Sr. | |
| 4,378,437 A | 3/1983 | Cook | |
| 4,391,705 A | 7/1983 | Cook et al. | |
| 4,648,968 A | 3/1987 | Cutler | |
| 4,710,292 A | 12/1987 | DeVos | |
| 4,945,756 A * | 8/1990 | Lewis et al. ................ | 73/49.2 |
| 5,092,482 A | 3/1992 | Wight et al. | |
| 5,238,844 A | 8/1993 | Wight et al. | |
| 5,384,033 A | 1/1995 | Matasovic | |
| 5,423,895 A | 6/1995 | Wight et al. | |

(Continued)

OTHER PUBLICATIONS

International Searching Authority, International Search Report, Dec. 17, 2008, 2 pages.

(Continued)

*Primary Examiner* — Mark Wendell
(74) *Attorney, Agent, or Firm* — Kolisch Hartwell, P.C.

(57) ABSTRACT

A method of ballasting a cover of a sludge digester that is comprised of a storage tank and the cover. The method includes placing a ballast into the storage tank in a first predetermined position, placing the cover onto the storage tank, lowering a lifting member of a lifting device through an access port in the cover and into the storage tank, securing the lifting member to the ballast, using the lifting device to lift the lifting member and the ballast until the ballast is in a second predetermined position that is substantially above the first predetermined position, engaging a support bracket attached to the cover with a support member; and securing the ballast to the cover with the support member while the ballast is in a third predetermined position that is substantially below the second predetermined position.

3 Claims, 3 Drawing Sheets

U.S. PATENT DOCUMENTS

| | | | | |
|---|---|---|---|---|
| 6,247,278 | B1 * | 6/2001 | Rysgaard | 52/192 |
| 6,451,206 | B1 * | 9/2002 | Charbonneau | 210/170.09 |
| 7,069,655 | B2 | 7/2006 | Lindbo | |
| 2004/0232148 | A1 | 11/2004 | Vera et al. | |
| 2006/0201876 | A1 * | 9/2006 | Jordan | 210/609 |
| 2006/0221766 | A1 | 10/2006 | Haughton | |

OTHER PUBLICATIONS

International Searching Authority, Written Opinion of the International Searching Authority, Dec. 17, 2008, 5 pages.

The International Bureau of WIPO, International Preliminary Report on Patentability, Mar. 24, 2010, 6 pages.

* cited by examiner

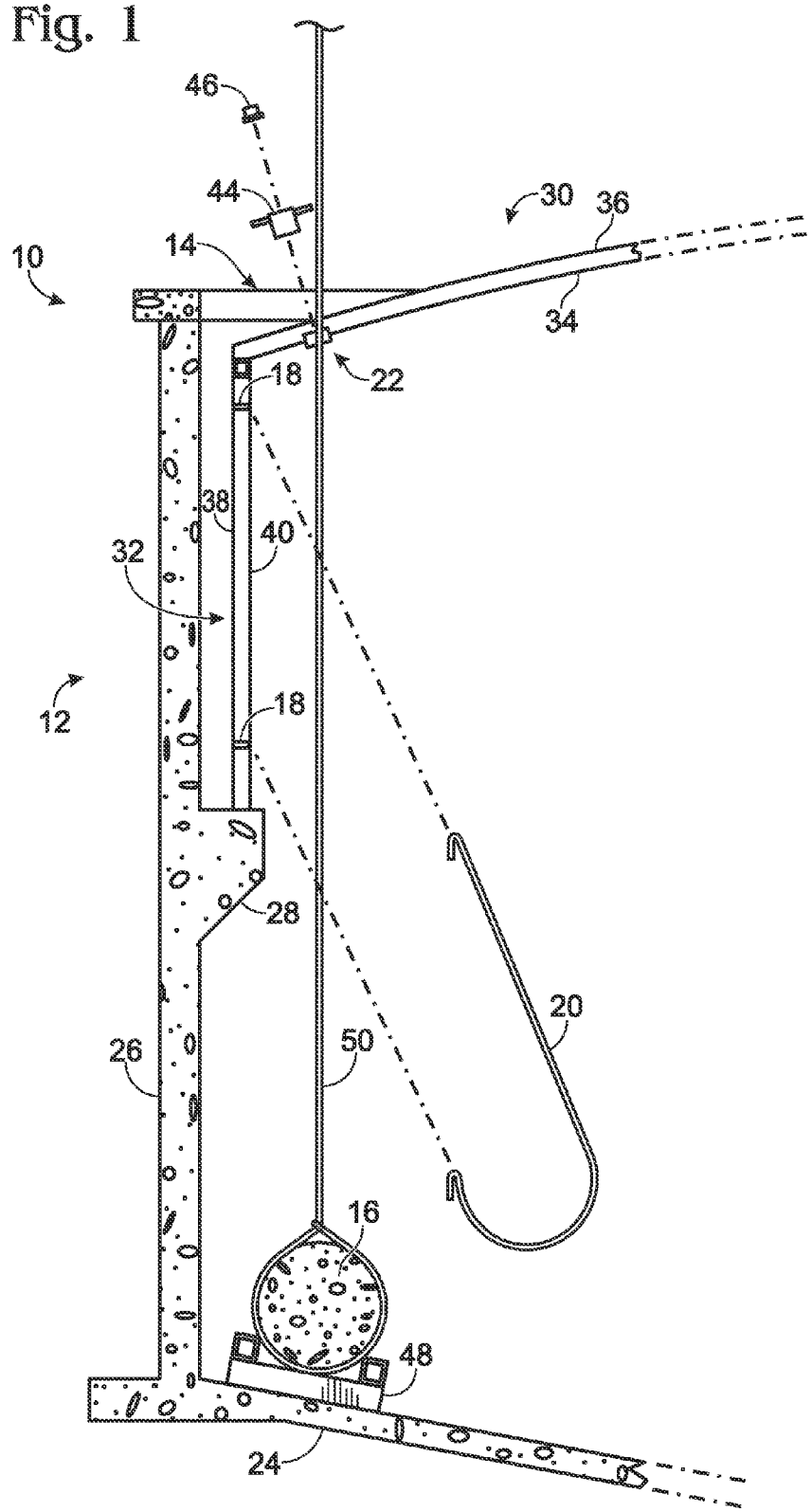

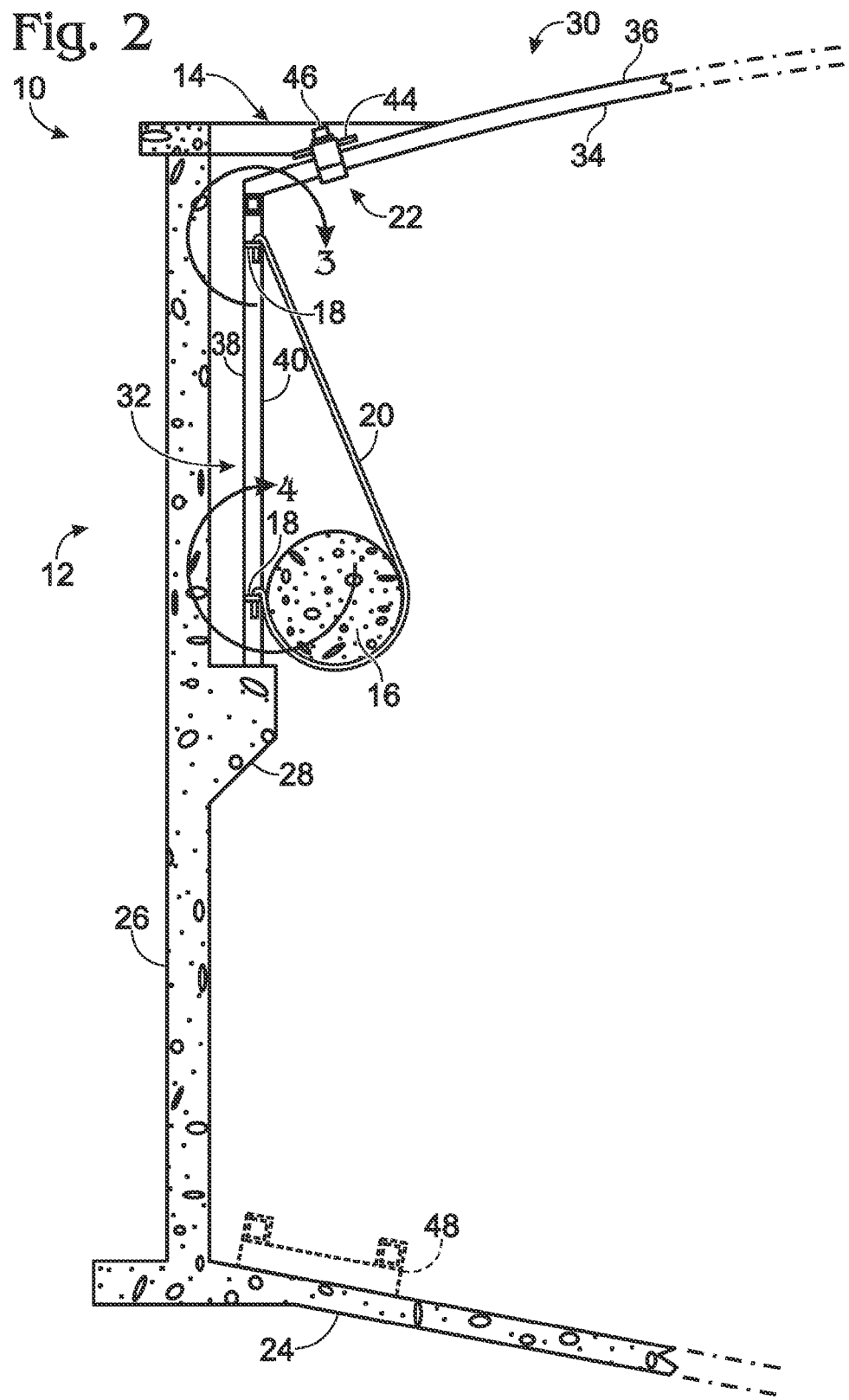

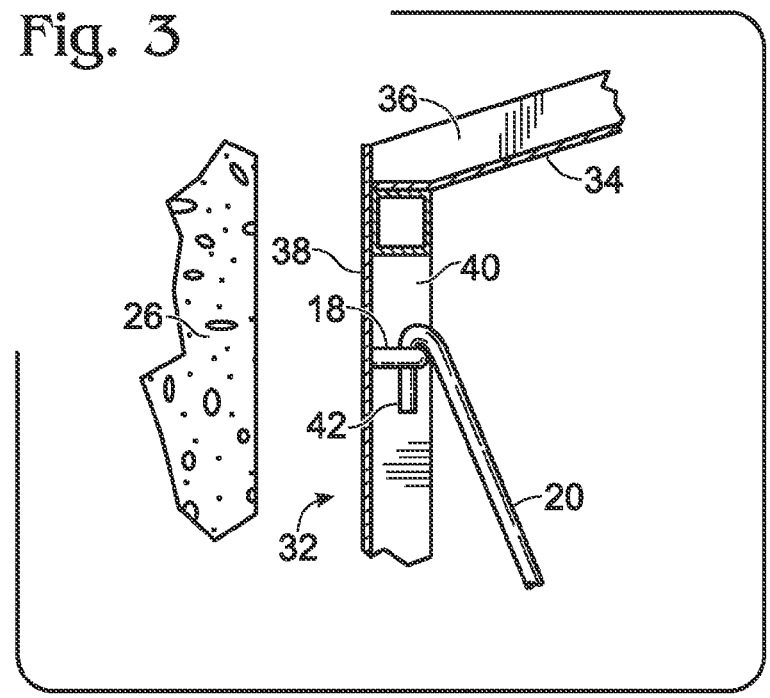
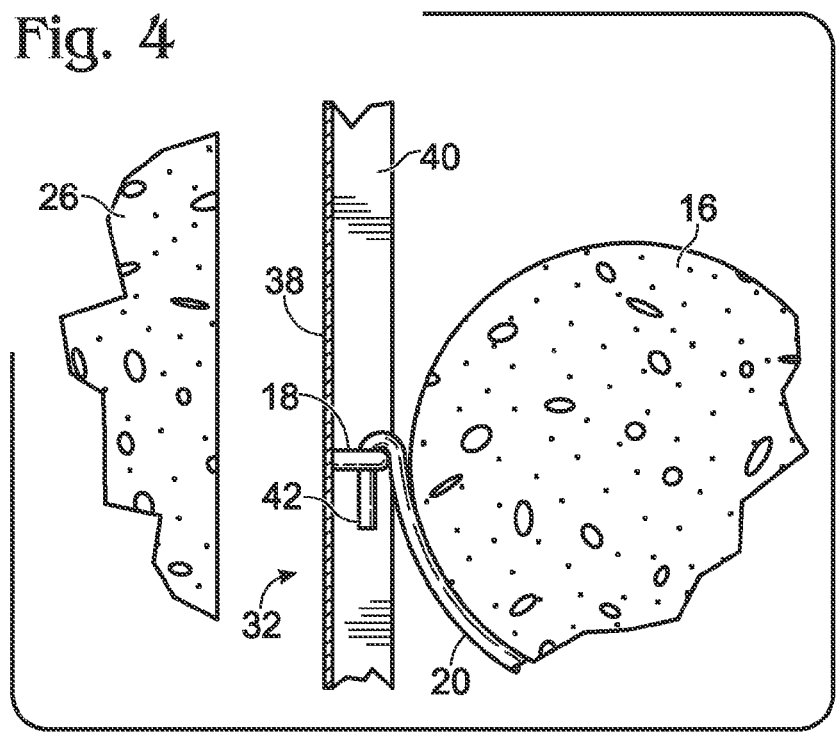

SYSTEMS AND METHODS FOR BALLASTING COVERS FOR GAS-HOLDING SLUDGE DIGESTORS

CROSS-REFERENCE TO RELATED APPLICATION

This application is a continuation of U.S. patent application Ser. No. 12/237,348, filed Sep. 24, 2008 and entitled "Systems and Methods for Ballasting Covers for Gas-Holding Sludge Digestors", which application claims priority under 35 U.S.C. §119(e) to U.S. Provisional Patent Application Ser. No. 60/974,758 entitled "Ballast Support System," filed Sep. 24, 2007, the complete disclosure of which is herein incorporated by reference for all purposes.

BACKGROUND

Sludge digesters typically include a storage tank for holding decomposing sludge, and a cover that contains, and floats on, an envelope of gas that is above, and generated by, the decomposing sludge. It is common to attach ballast to the cover to increase the weight of the cover, and the pressure of the gas within the digester. The pressure of the gas within the sludge digester is proportional to the effective weight of the ballasted cover. Examples of gas-holding storage tanks, such as sludge digesters, are found in U.S. Pat. Nos. 251,245; 1,989,589; 2,050,686; 2,050,915; 2,373,797; 3,187,897; 3,288,295; 3,535,236; 4,060,175; 4,378,437; 4,391,705; 4,648,968; 4,710,292; 5,092,482; 5,238,844; 5,384,033; 5,423,895; 6,247,278; 7,069,655; and U.S. Patent Application No. 2004/0232148, the disclosures of which are hereby incorporated by reference in their entirety for all purposes.

Most sludge digesters that include a ballasting system for the cover include horizontal support shelves that are attached and orthogonal to the lower end of the cover's side skirt, and that extend inwardly from the side skit toward the center of the storage tank. These support shelves are generally welded into place after the cover has been constructed and placed on top of the storage tank. In order to attach the ballasts to the support shelves, the ballasts must be lifted vertically from the base of the tank to a height that is greater than the support shelves, moved horizontally to a position above the support shelves, and then lowered onto the support shelves. The ballast is then secured to the support shelves where they are supported during operation of the digester.

This process presents a number of problems. First, because the support shelves are welded to the lower end of the side skirt after the cover is placed onto the storage tank, the support shelves and portions of the side skirt must be painted, while the cover is on the storage tank, so as to inhibit corrosion of the otherwise unpainted portions of the cover in the highly corrosive environment within an operating sludge digester. This is often very difficult, and costly, because some of the portions of the cover that need to be painted are not readily accessible, due to the tight fit between the side skirt and the outer wall of the storage tank. Some portions of the cover may not be painted effectively, thus increasing the risk of corrosion.

Second, because the ballasts must be lifted vertically, moved horizontally and lowered vertically in order to be secured to the support shelves, the ballasts must be moved in such a manner using either (a) a make-shift pulley system within the storage tank, which is difficult to use and construct due to the extreme weight of the ballasts, or (b) a crane or other lifting device that can only move the ballast onto the support shelves if the roof includes a elongated radial opening in its roof that permits the crane to lower and raise its cable or other lifting member vertically, and to move the ballast horizontally relative to the support shelf. If a lifting device is used through an elongate opening in the roof of the cover, then after the ballast is secured to the support shelf, and prior to operation of the digester, the opening must be sealed, such as by welding cover plates over the openings, to ensure that the cover is gas-tight.

Third, moving the ballast horizontally and vertically relative to the support shelves during installation of the ballasts creates a risk that the ballast will scrape paint off of the support shelves or the side skirt, which increases the risk that the support shelf will corrode and eventually fail. These problems are alleviated by the invention disclosed herein.

BRIEF DESCRIPTION OF THE DRAWINGS

FIG. 1 is a cross-sectional view of a sludge digester having a storage tank a cover, and a system for ballasting the cover in a non-ballasting configuration.

FIG. 2 is a cross-sectional view of the sludge digester of FIG. 1, with the system for ballasting the cover in a ballasting configuration.

FIG. 3 is a cross-sectional view of a first support bracket engaged with a support member.

FIG. 4 is a cross-sectional view of a second support bracket engaged with the support member of FIG. 3.

DETAILED DESCRIPTION

The present invention relates to systems and methods for ballasting covers for gas-holding sludge digesters having a storage tank and a cover. FIGS. 1 and 2 show a sludge digester 10 having a storage tank 12, a cover 14 and a system for ballasting the cover that includes a ballast 16, one or more support brackets 18 attached to the cover, a support member 20 for selectively engaging one or more support brackets, and a selectively sealable access port 22 in the cover.

The storage tank 12 may include a bottom wall 24 with a cylindrical vertical side wall 26 extending upwardly from the bottom wall. In the embodiment shown in FIGS. 1 and 2, bottom wall 24 has an inverted conical shape although other shapes could be used. The inverted conical shape allows the heavier materials, e.g. grit, fully digested material, to accumulate in a central position for removal. Mounted along the interior of the side wall is a series of corbels 28 projecting inwardly toward the center of the storage tank. The corbels could also be formed as a continuous projection around the interior of the side wall. Typical sludge digester storage tanks are made of concrete materials, although other materials, such as ceramics, metals, and fiberglass may be used. Generally, the storage tank is formed prior to installation with the corbels in place.

The cover 14 is dimensioned to fit onto the storage tank 12, and as such, the cover is designed and manufactured when the dimensions of the storage tank are known. These dimensions include the diameter of the storage tank, the height of the side walls 26, the height of the corbels 28 above the bottom wall 24, the volume and pressure of gas that must be accommodated by the digester, and the high and low liquid levels in the storage tank. The cover may include a substantially dome-shaped roof 30 and an annular or cylindrical side skirt 32 extending downwardly from the top wall.

The roof 30 of the cover 14 may be constructed of a plurality of pie shaped panels 34 separated and connected by radial beams 36, or ribs, that reinforce the structure of the roof, where the number and size of the panels and radial beams depends on the size of the storage tank and cover. The roof panels and radial beams may be connected using any suitable fastening means, such as nuts and bolts, and/or welding.

Side skirt 32 may be constructed of a plurality of arc-shaped panels 38 reinforced by a plurality of stiffeners 40, where the number and size of the panels and stiffeners depends on the size of the storage tank and the length of the side skirt. The length of the side skirt is dependant on the height of the corbels 28 above the bottom wall 24, and the volume and pressure of gas that must be accommodate by the digester 10, and must be sufficient to maintain the liquid seal with the liquid within storage tank 12. When the cover 14 is placed onto the storage tank, as shown FIGS. 1 and 2, the lower end of the side skirt rests atop the corbels, thereby preventing the side skirt from resting on the bottom wall 24. Additionally, guide rollers (not shown) may be mounted on the tank side of the side skirt to guide the cover while it moves vertically during operation of the digester and to maintain the cover in a substantially central position within the storage tank. Such guide rollers may prevent the cover from tipping and becoming wedged within storage tank.

The cover 14, including the roof 30, the side skirt 32, and any additional structures associated with the cover, may be made of any suitable material, including stainless steel, steel, fiberglass, carbon fiber, etc., although any suitable material can be used.

As discussed above, the system for ballasting the cover may include a ballast 16, one or more support brackets 18 attached to the cover, a support member 20 for selectively engaging one or more support brackets, and a selectively sealable access port 22 in the cover. Generally, the ballast will be made of concrete, although other materials may be used. The ballast may be any suitable size, shape and weight. In one embodiment, the ballast may be cylindrical concrete ballast, which is pre-formed and commercially available, thus preventing the need to create a mold and pour the concrete ballast during assembly of the digester 10.

The support brackets 18 may include any structure attached to the cover 14 that can be securely engaged by the support member 20 and has sufficient strength to bear some or all of the weight of the ballast 16 when the ballasting system is in a ballasting configuration (i.e. when the support member is engaged with the support bracket and is bearing the weight of the ballast in a manner that secures the ballast to the cover). As shown in FIGS. 1-4, for example, upper and lower support brackets may be attached to the cover 14. As shown, both the upper and lower support brackets may be attached to the side skirt 32, although the upper support bracket may also be attached to the roof 30. The support bracket may be L-shaped, as shown in FIGS. 1-4, with one end attached to an arc-shaped panel 38 and the other end to a stiffener 40. Alternatively or additionally, some support brackets may be U-shaped with each end attached to an arc-shaped panel, or to a stiffener. In embodiments where the upper support bracket is attached to the roof, the upper support bracket may be attached to a pie-shaped panel 34 or any other suitable structure. Each support bracket also may be a circular hole akin to an eye-hook and attached to the portions of the cover described above. In some embodiments, and as discussed below, only a single support bracket may be provided to be engaged by a particular support member, where in such cases, the support member may include multiple portions selectively engageable and disengageable from that support bracket, or the support member includes a first portion fixedly attached to the cover, and a second portion selectively engageable and disengageable from the support bracket.

The support member 20 may include any high-strength structure for selectively engaging and disengaging one or more of the support brackets 18 attached to the cover 14, and further for supporting the weight of the ballast 16 in a manner that secures the ballast to the cover 14 when the ballasting system is in a ballasting configuration. For example, as shown in FIGS. 1 and 2, the support member may be a substantially rigid structure that includes a portion having a shape that is complimentary to the shape of the ballast. In the case of cylindrical ballast, a rigid support member may therefore include a portion that is substantially arc shaped, and that has a radius of curvature complimentary to the radius of curvature of the cylindrical ballast. Rigid support structures may be constructed of steel, aluminum, stainless steel, or any other suitable material with sufficient strength and rigidity to support the eight of the ballast, and may include plates, bars, angles, channels, beams, or any other suitable type of material. The support member may also be a flexible structure, such as a cable, wire, or chain that has a portion that contacts and supports the weight of the ballast during securement to the cover. As shown in FIG. 2, when the ballasting system is in a ballasting configuration, the support member may at least partially wrap around a bottom portion of the ballast to support its weight. The support member may be painted to inhibit corrosion during operation of the digester.

The support member 20 may include one or more engagement members 42 for engaging the one or more support brackets 18 attached to the cover 14. For example, as shown in FIGS. 1-4, a support member may have two ends, and may include two engagement members 42, one at each end, although the engagement members may be positioned at any suitable location on the support member. Each engagement member may be a hook, clip, bolt, etc. for selectively engaging and disengaging a support bracket. Engagement members may be integral with the rest of the support member, or may be separate structures coupled or attached to the rest of the support member. As shown in FIGS. 1-4, each engagement member may be adapted to attach to a different support bracket such as an upper and a lower support bracket. In some embodiments, only a single bracket attached to the cover may be provided for a particular support member, where in such cases, the support member may include one or more engagement members that are each selectively engageable and disengageable from that support bracket, or the support member includes a first portion fixedly attached to the cover, and a second portion selectively engageable and disengageable from the support bracket.

Although the discussion above only refers to a single support member 20 for use in securing a particular ballast 16 to the cover 14, it should be appreciated that a plurality of support members may be used to secure a particular ballast to the cover. Each support member may engage support brackets attached to the cover in accordance with the above disclosure. For example, if two support members are used to secure a ballast to the cover, and each support member includes a pair of engagement members 42, then up to four support brackets 18 (two upper and two lower support brackets) may be necessary to secure the ballast to the cover. Moreover, a plurality of ballasts may be secured to a particular cover, where each ballast is secured to the cover with one or more support members, and each support member requires one or more support brackets.

Because the ballasting system of the present invention does not include a support shelf, a ballast 16 may be secured to the cover 14 by vertically raising the ballast, such as with a crane or other lifting device, from a first position to a second position directly or substantially above the first position, where the support member 20 can be wrapped around the ballast and secured to one or more support brackets 18. The lifting device can then be used to lower the ballast slightly until the weight of the ballast settles into the support member, and gravity pulls the support member and each engagement member 42 tightly against each support bracket 18. After the weight of the ballast has settled into the support member, the ballast may be in a third position directly or substantially, (albeit slightly) below the second position.

In order to enable the aforementioned movement of the ballast 16 without the need (a) for make-shift pulley systems, and (b) to cut a hole in or disassemble the cover, or (c) to attempt to remove the cover with the ballast attached, the ballast support system includes access ports 22 in the roof 30 of the cover 14. These access ports provide access to the ballast 16 with a lifting device. Each access port may be substantially or directly above the position where the ballast 16 is secured to the cover when the ballasting system is in a ballasting configuration (see FIG. 2). The access port may be selectively sealable and unsealable so as to selectively provide access to the ballast at any desired time. For example, the access port may include an access port protector 44 and an access port plug 46. The access port protector 44 may be welded or otherwise attached to the access port and may be internally threaded. The access port plug 46 may be likewise threaded so that it can be engaged with the access port protector in an air-tight manner, and selectively disengaged from the access port-protector to provide access to the storage tank 12. As such, the hole in the access port that provides access into the tank may be circular or cylindrical, and may have a diameter sufficient to fit any desired lifting member (such as a hook, cable, chain, etc.) of a lifting device therethrough. Provided the access port is substantially above the position where the ballast is secured to the cover, the access port may also be any other size shape and configuration that permits selective sealing and unsealing of the access port, and that permits a lifting device to be inserted therethrough.

The system for ballasting the cover described above eliminates the need for welding a support shelf to the bottom of the side skirt 32, and for painting the support shelf and/or side skirt after such a welding process. The system also reduces the risk that the ballast 16 will scrape paint off portions of the cover, thereby decreasing the risk of corrosion and failure. Finally, the system provides a substantially more efficient means for performing a method of attaching and detaching ballast to the cover.

For example, as shown in FIGS. 1 and 2, a method of ballasting a cover 14 of a sludge digester 10 may include placing a ballast 16 into the storage tank 12 in first a predetermined position that is substantially or directly below a position where the ballast will be secured by the support member 20 to the cover, such as on a platform or base 48 sitting on the bottom wall 24. After the ballast is inserted into the storage tank, the cover may be placed onto or assembled on the storage tank. A lifting member 50 (such as a cable, hook, etc.) of a lifting device (such as a crane) may then be lowered through an access port 22 in the roof 30. The access port may be substantially or directly above the first predetermined position and/or the position where the ballast will be secured to the cover. After lowering the lifting member through the access port, the lifting member may be secured to the ballast (See FIG. 1). The lifting device may then be used to lift the lifting member and the ballast until the ballast is in a second predetermined position that is substantially or directly above the first predetermined position and/or the position where the ballast will be secured to the cover. Once the ballast is in position for engagement of the support member, the support member may be engaged with one or more support brackets 18 in accordance with the above disclosure, such as with one or more engagement members 42. The lifting device can then be used to lower the ballast slightly until the weight of the ballast settles into the support member, and gravity pulls the support member and each engagement member tightly against each support bracket. After the weight of the ballast has settled into the support member, the ballast is in its ballasting position, and the ballasting system is in a ballasting configuration. The ballasting position of the ballast may be directly or substantially, (albeit slightly) below the second position, and directly or substantially below the access port. (See, e.g. FIG. 2). After the ballasting system has been configured in the ballasting configuration, the lifting member 50 may be disengaged from the ballast 16, and the lifting device may be used to lift the lifting member 50 through the access port 22 and out of the storage tank 12. The access port may then be sealed with a removable sealing mechanism, such as with access port plug 46. The digester 10 is then ready to be operated.

If the digester 10 is ever in need of maintenance or repair, and/or if the cover 14 ever needs to be removed from the storage tank 12, then the ballast system described herein readily allows for removal of the ballast 16 from the cover. First, the removable sealing member may be removed from the access port 22, thereby unsealing the access port. A lifting member 50 may then be lowered through the access port and into the storage tank and secured to the ballast. The lifting device may be used to lift the lifting member and the ballast slightly to remove the gravitational force applied by the ballast on the support member 20. The support member then may be unsecured from the cover, such as by disengaging the one or more engaging mechanisms 42 from the one or more support brackets 18. The lifting device may then be used to lower the lifting member and the ballast to the ground (such as onto a base or platform 48 on bottom wall 24), where the lifting member is disengaged from the ballast. Once the ballast has been removed from the cover, the lifting member can be removed from the storage tank through the access port. In some cases, once the ballast has been removed, the cover may be form the storage tank removed in its fully constructed.

Accordingly, while embodiments of methods and systems have been particularly shown and described with reference to the foregoing disclosure, many variations may be made therein. Various combinations and sub-combinations of features, functions, elements and/or properties may be used. Such variations, whether they are directed to different combinations or directed to the same combinations, whether different, broader, narrower or equal in scope, are also regarded as included within the subject matter of the present disclosure. The foregoing embodiments are illustrative, and no single feature or element is essential to all possible combinations that may be claimed in this or later applications. The claims, accordingly, define selected inventions disclosed in the foregoing disclosure. Where the claims recite "a" or "a first" element or the equivalent thereof, such claims include one or more such elements, neither requiring nor excluding two or more such elements. Further, ordinal indicators, such as first, second or third, for identified elements are used to distinguish between the elements, and do not indicate a required or limited number of such elements, and do not indicate a particular position or order of such elements unless otherwise specifically stated.

We claim:

1. A method of ballasting a cover of a sludge digester that is comprised of a storage tank and the cover, the method comprising:

placing a ballast into the storage tank in a first predetermined position;

placing the cover onto the storage tank;

lowering a lifting member of a lifting device through an access port in the cover and into the storage tank;

securing the lifting member to the ballast;

using the lifting device to lift the lifting member and the ballast until the ballast is in a second predetermined position that is substantially above the first predetermined position;

engaging a support bracket attached to the cover with a support member; and securing the ballast to the cover by at least partially wrapping the support member around a bottom portion of the ballast while the ballast is in a third predetermined position that is substantially below the second predetermined position.

2. The method of claim 1, wherein the support member includes a clip adapted to engage the support bracket with the support member.

3. The method of claim 1, further comprising:

disengaging the lifting member from the ballast;

selectively engaging a threaded cover of the sealing member with a threaded hole formed in the access port;

using the lifting device to lift the lifting member through the access port and out of the storage tank; and sealing the access port with a removable sealing member.

* * * * *